United States Patent [19]

Saimoto et al.

[11] Patent Number: 4,572,001
[45] Date of Patent: Feb. 25, 1986

[54] METHOD AND APPARATUS FOR MEASURING THERMODYNAMIC RESPONSE

[75] Inventors: Shigeo Saimoto, Kingston; Zbigniew Basinski, Gloucester, both of Canada

[73] Assignee: Queen's University at Kingston, Kingston, Canada

[21] Appl. No.: 575,274

[22] Filed: Jan. 30, 1984

[51] Int. Cl.⁴ ............................................. G01N 3/00
[52] U.S. Cl. ...................................... 73/765; 73/805; 73/826
[58] Field of Search ................. 73/765, 805, 760, 788, 73/822, 825, 818, 826, 847, 840

[56] References Cited

U.S. PATENT DOCUMENTS

3,411,345 11/1968 Wintriss ................................. 73/760
4,012,953 3/1977 Ormond ................................. 73/765
4,030,347 6/1977 Norris et al. .......................... 73/805
4,432,240 2/1984 Adams ................................... 73/822

Primary Examiner—Anthony V. Ciarlante
Attorney, Agent, or Firm—Richard J. Hicks

[57] ABSTRACT

A method and apparatus for precisely controlling plastic strain rate during plastic deformation testing of a solid material such as a metal or plastic are described in which the effects of elastic strain rates associated with the specimens and machines used for such testing are eliminated by applying corrections proportional to the load on the specimen. Thus strain rate sensitivity, unaffected by the machine or specimen modulus can be measured. Strain rate sensitivity can be used to measure the activation volume of the specimen which may be used for quality control of material processing and/or manufactured articles.

7 Claims, 12 Drawing Figures

METHOD AND APPARATUS FOR MEASURING THERMODYNAMIC RESPONSE

FIELD OF INVENTION

This invention relates to a method and apparatus to precisely measure the thermodynamic response of non-elastic deformation in solid materials during plastic deformation and in particular uniaxial testing thereof.

BACKGROUND OF INVENTION

The thermodynamic response of materials during plastic deformation originates from the imposed plastic strain rate. Thus the precise thermodynamic parameter has to be measured during changes in the plastic strain rate. The method described herein permits this desired controlled plastic strain rate change. Even the most sophisticated materials testing system currently available permits only total strain rate changes, that is the changes in the sum of the plastic and elastic strain rate of the specimen to be determined. The following analysis illustrates that the thermodynamic parameter, the activation volume, v is determined by performing plastic strain rate change tests. Furthermore, it will show how the elastic strain of the specimen and the frame of the testing apparatus which interferes with the plastic strain rate change is removed by the proposed method.

All solids which are deformed in a non-elastic manner under an applied stress $\sigma$ are aided in the microplastic deformation process by the thermal energy. The most simple analytical form in which this stress-aided process can be described is by the rate equation $$\dot{\epsilon} = \epsilon_o \nu \exp \frac{-(\Delta G - v\sigma)}{kT}$$

where $\dot{\epsilon}$ is the enforced plastic strain rate; $\epsilon_o$, the number of strain centres which can participate in the deformation process; $\nu$, the frequency of attempts to overcome the obstacle preventing the incremental strain process from taking place; $\Delta G$, the total free energy required to overcome the obstacle at 0° K.; v, the activation volume; k, the Boltzmann constant, and T, the test temperature in Kelvin.

Thus $$\frac{\partial \ln \dot{\epsilon}}{\partial \ln \sigma}\bigg|_T = \frac{\partial \ln \epsilon_o}{\partial \ln \sigma}\bigg|_T + \frac{\partial \ln \nu}{\partial \ln \sigma}\bigg|_T + \frac{1}{kT}(v\sigma)$$

Hence experimental v can be defined as $$v = kT \frac{\partial \ln \dot{\epsilon}}{\partial \sigma} = \frac{k}{\sigma S}$$

where S is called the strain rate sensitivity and defined as $$S = \frac{1}{T} \frac{\partial \ln \sigma}{\partial \ln \dot{\epsilon}}\bigg|_T$$

This value is identical to the theoretical one if the first two terms of the right side are zero. If these terms are not zero, their temperature and strain rate dependence can reveal the atomic/molecular processes responsible for the deviation. The above definition of v shows that, ideally, the change in stress value $\sigma_1$ at $\dot{\epsilon}_1$ to $\sigma_2$ can be measured at $\dot{\epsilon}_2$ if an instantaneous plastic strain rate change is made. Thus the change $\Delta\sigma$ is an elastic response of the microplastic process, that is if $\dot{\epsilon}_2 < \dot{\epsilon}_1$ then the stress can be lowered just enough so that the reduction in $$\frac{e^{-(\Delta G - v\sigma)}}{kT}$$

is in the same ratio as that for the plastic strain rate $\dot{\epsilon}$.

In practice, however, tensile testing machines and systems and the specimens used therein have an elastic response which generally completely masks the reduction in stress effect. The stress change is given by $$\Delta \sigma = \frac{-kT}{v} \ln \frac{\dot{x}_1}{\dot{x}_2} \text{ where}$$

$\dot{x} = \dot{\epsilon} L + \dot{\sigma} L (1/E + 1/M)$. $\dot{x}$ is the displacement rate (the change in distance between the grips of the specimens) and is the parameter usually controlled by the operator; v, the activation volume; $\dot{\epsilon}$, the plastic strain rate; L, the current specimen length; E, the Young's Modulus of the specimen; M, the machine stiffness component including the linkages (the effective spring constant of the loading train).

In order to achieve plastic strain rate changes, $\dot{x}$ must be made equal to $\dot{\epsilon}$ by imposing $\dot{\sigma}L(1/E + 1/M)$ to become zero.

OBJECTS OF INVENTION

Thus, an object of the present invention is to provide a method to permit this controlled plastic strain rate change by using for example a servo-hydraulic materials testing system.

Another object of the present invention is to provide a materials testing apparatus for effecting an instantaneous plastic strain rate change.

Thus, by one aspect of the invention there is provided a method for precisely controlling plastic strain rate during plastic deformation testing of a solid material, wherein effects of elastic strain rates associated with such testing are eliminated by applying corrections proportional to the load on the specimen.

By another aspect of the invention there is provided an apparatus for precisely controlling plastic strain rate during plastic deformation testing of a solid material comprising:
  means to apply a controlled plastic strain to said specimen; and
  means to effect a plastic strain rate change to said specimen while eliminating effects of elastic strain.

DESCRIPTION OF DRAWINGS

The invention will be described in more detail hereinafter with reference to the accompanying drawings in which.

DETAILED DESCRIPTION OF PREFERRED EMBODIMENTS

The essence of the invention can be elucidated in the following manner.

Figure 1:
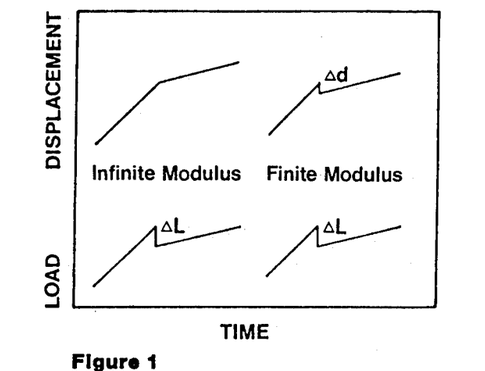
FIG. 1 is a schematic graph illustrating load respose under displacement control with (a) a specimen of infinite modulus and (b) a specimen of finite modulus.

Consider an ideal test system where machine effects are absent and the material is ideally plastic with constant istropic hardening, i.e. one which possesses an infinite modulus and a constant work hardening coefficient independent of strain rate. If a plastic strain rate change is imposed, a displacement device attached to the specimen should respond as schematically illustrated in FIG. 1 (infinite modulus). If, however, the specimen has a finite elastic modulus while still maintaining displacement control, the displacement path would have to be adjusted to compensate for the elastic contraction of the specimen due to the imposed load change, since $\Delta d = 1\Delta L/AE$; A being the current cross-sectional area and 1, the current specimen length. Hence the modified displacement control is required, as depicted in FIG. 1 (finite modulus). If such a strain control can be enforced, the load response can be monitored and the change of work hardening coefficient with strain can be determined. For finite values of M where $1/M >> 1/E$, the $\Delta d'$ of the load train (or the hydraulic ram for an electro-hydraulic system) is much larger, $\Delta d' >> \Delta d$. However since the ram is being controlled by the extensometer attached to the specimen the ram will move the required $\Delta d'$ to produce the necessary $\Delta d$ in the specimen.

Examples of the success of this method using a modified screw driven machine are given below.

Figure 2:
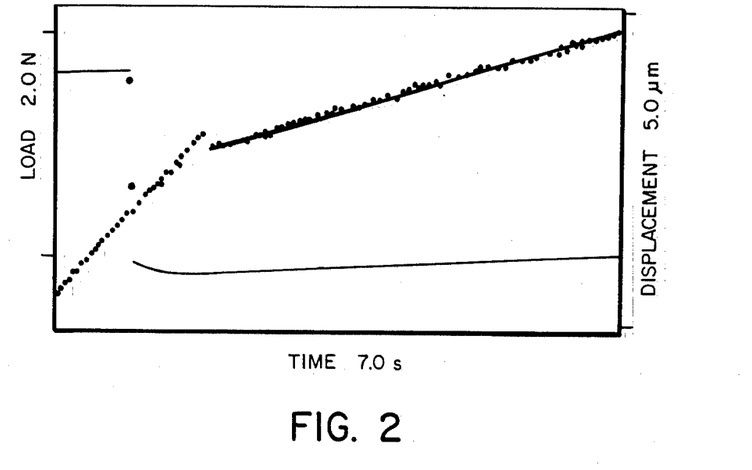
FIG. 2 is a graph illustrating load response under displacement control for an aluminum specimen tested at $1.5 \times 10^{-4}/S$ at 21° C. when a plastic strain rate change of $\frac{1}{4}$ was imposed. The curves are displaced for clarity.
Figure 3:
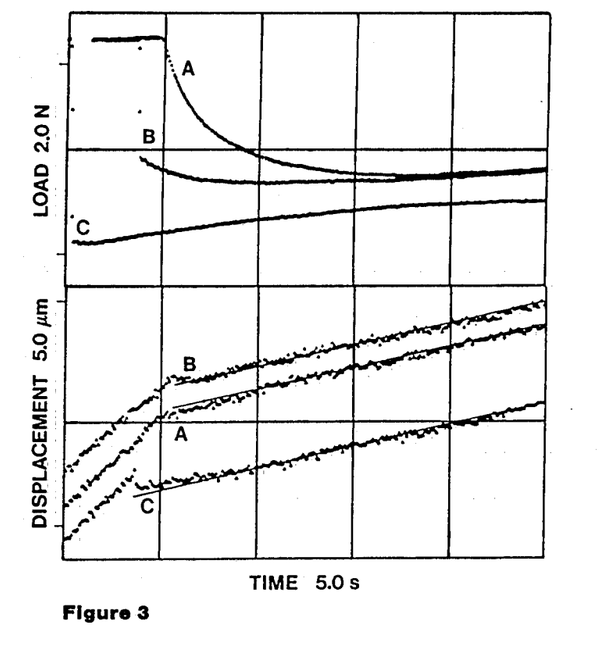
FIG. 3 is a graph illustrating examples of ¼ rate changes on (a) load response and (b) displacement response for an aluminum sample tested at $1.5\times10^{-4}$/S at 21° C., for the cases (A) not compensated, (B) slightly under-compensated and (C) considerably over-compensated.

FIG. 2 illustrates the actual test results achieved while testing an aluminum specimen at $1.5\times10^{-4}$/S at 21° C. when a rate of change of ¼ is imposed. Note that, by imposing a step in the displacement-time plot as suggested by FIG. 1 (finite modulus), a load response equivalent to $\Delta\sigma$ unaffected by the machine or specimen modulus can be measured. Without this step the details of the microstructural processes within 2 seconds of change in strain rate are lost as seen in FIG. 3 which illustrates an uncompensated (A), slightly compensated (B) and considerably over-compensated (C) displacement and load response in an aluminum test piece tested under the same conditions as specified for FIG. 2. The size of the steps depends on the material, strain rate and temperature. Thus it is a variable to be determined by the operator. In a computer controlled system it is possible to set the size of the step by first performing several strain rate changes without this correction and estimating v. In subsequent changes, the step can be calculated using the approximate v and by iteration one can achieve ideal compensation.

Figure 8:
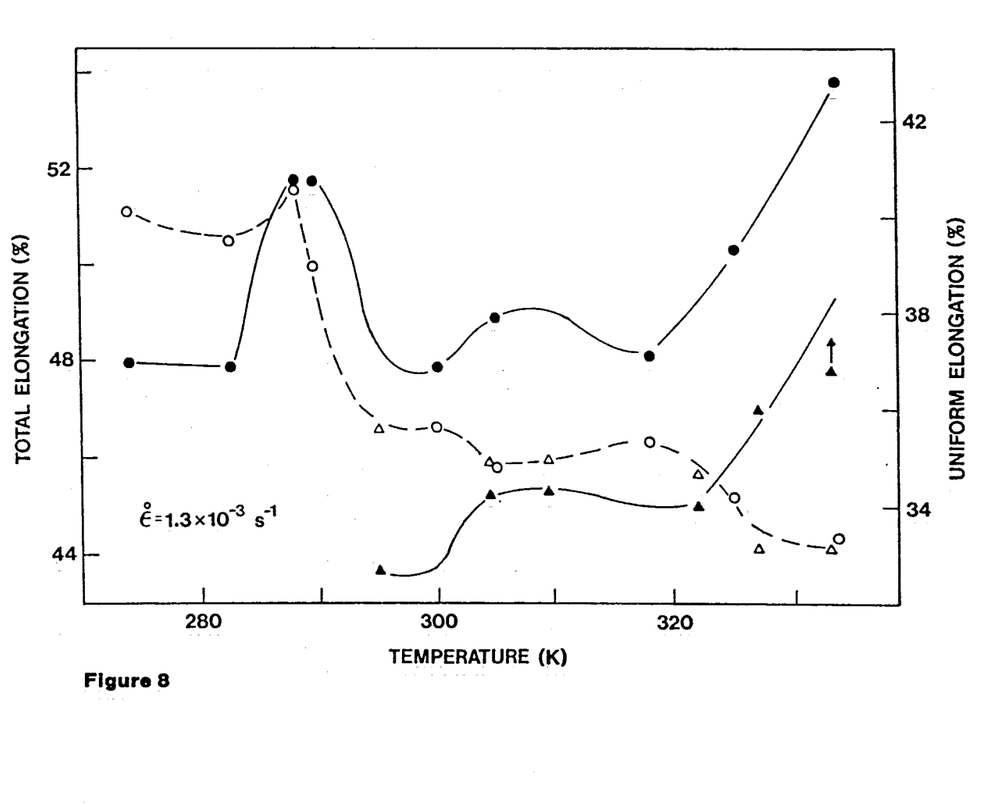
FIG. 8 is a graph of total elongation and uniform elongation versus temperature for two sets of aluminum samples.

A most useful application of precise strain rate sensitivity measurement as a function of strain rate and temperature is in the assessment of the formability of metal sheets. The plastic strain rate sensitivity is the most important factor in extending geometrical stability of tensile specimens after the work hardening has decreased to a value at which it no longer can compensate for the decrease in area. From the Considéré condition $$\left(\frac{d\sigma}{d\epsilon} = \sigma\right)$$

at the position of tensile instability (at the ultimate tensile stress UTS), it can be deduced that, at least for aluminum, $$\left.\frac{\partial\ln\sigma}{\partial\ln\epsilon}\right|_{T,UTS} = C\left.\frac{\partial\ln S}{\partial\ln\epsilon}\right|_T \dot{\epsilon}\exp\frac{Q}{kT}$$

where $\dot{\epsilon}$ is the imposed plastic strain rate, Q the activation energy of the dynamic recovery process during the deformation and C is a material constant. This result is significant since the diffuseness of the neck is highly dependent on the strain rate sensitivity. The greater the degree of diffuseness of the neck prior to rupture the better is the sheet formability of the material. In the case of aluminum the S($\dot{\epsilon}$) vs T curves indicate that a diffuse necking peak should occur about 16° C. This prediction is confirmed as shown in FIG. 8 when the total elongation (filled circles and triangles) is taken as a measure of diffuse necking. Uniform elongation (open circles and triangles) is shown for comparison.

Figure 4:
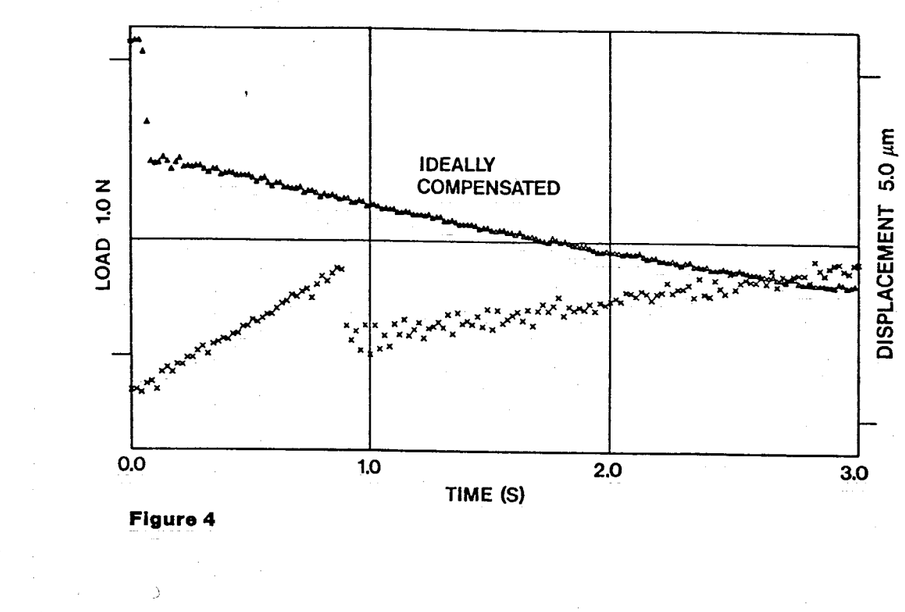
FIG. 4 is a graph illustrating load and displacement change for almost ideal compensation during strain rate change for ¼ for polyethylene tested at $1.5\times10^{-4}S^{-1}$ at 20° C.
Figure 5:
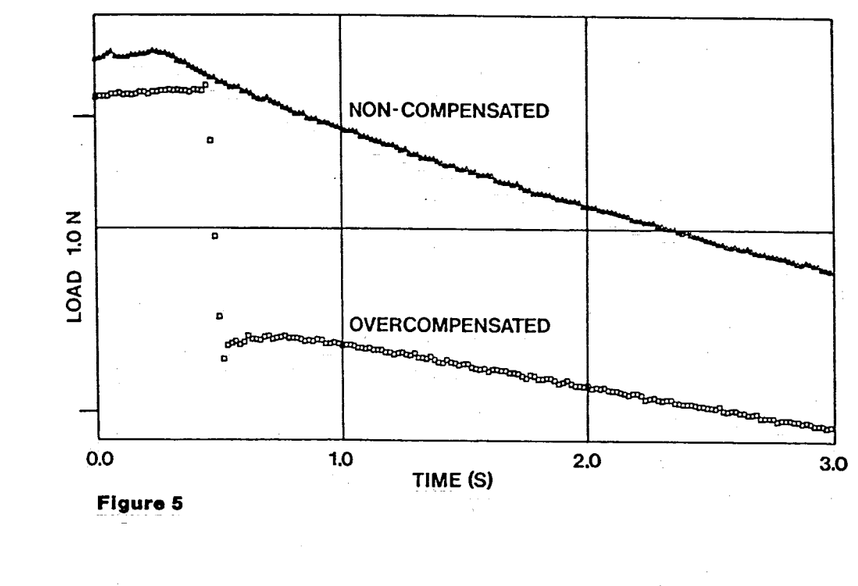
FIG. 5 is a graph similar to FIG. 4, illustrating load change for non-compensation and over-compensation for polyethylene tested under the same conditions as for FIG. 4.

As noted, in all the above examples aluminum was used. Similar procedures can be performed for thermoplastic materials such as polyethylene, as shown in FIG. 4. In this case, however, due to a large dynamic recovery, the activation volume without this compensation or step-ramping is not measurable since the time for the load-time slope to become positive is very long. The negative slope due to dynamic recovery inhibits extrapolation to determine an appropriate v. In comparison with the uncompensated case in FIG. 5, the ideally compensated one of FIG. 4 shows that it is possible to determine the stress response which becomes obliterated at time over 0.3 s. Nuclear magnetic resonance techniques used by other investigators have shown two relaxation times of ~0.3 s and ~30 m in polyethylene which correlates excellently with the data noted herein.

The application of this technique to polymers is useful to reveal the mechanisms of deformation of polyethylene and step-ramping strain rate testing may be used for quality control of manufactured high density polyethylene pipe and for the assessment of new experimental resins.

In all of the experiments thus far described the stress response due to the step-ramping was performed on a screw driven tensile machine, and was effected by placing an electromagnet in the loading train so that upon strain rate change a simultaneous $\Delta d'$ was imposed by the electromagnet.

Figure 6:
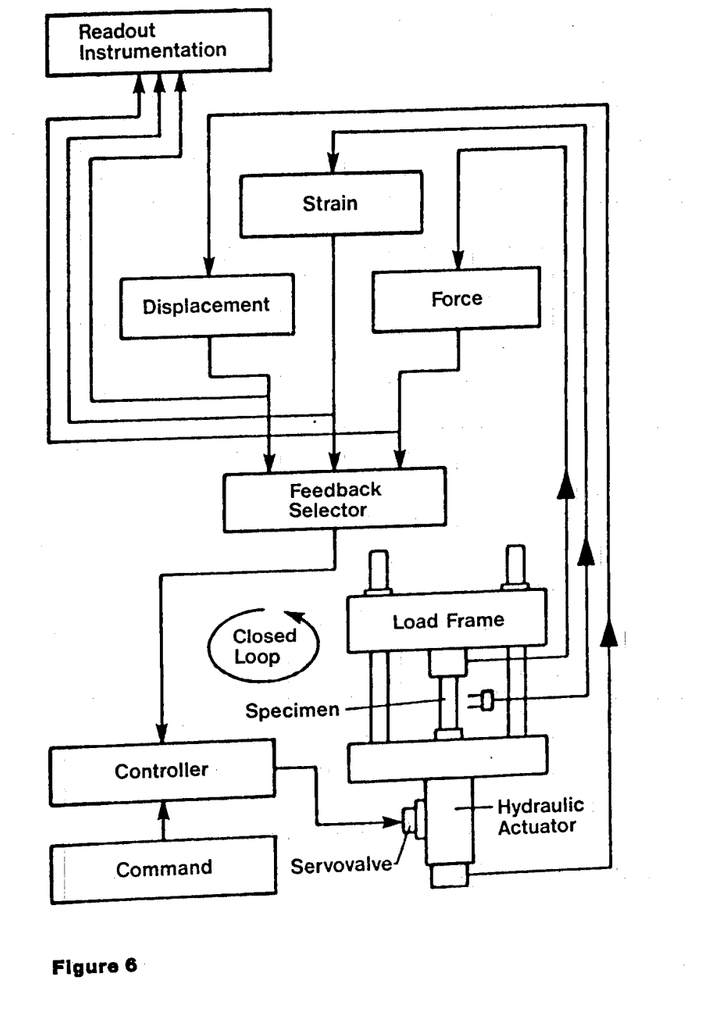
FIG. 6 is a block diagram illustrating a typical load testing system for use in the present invention showing the location of the command module.

In a more preferred embodiment, however, the step-ramping may be accomplished by an electro-hydraulic system controlled by a servo system. Systems heretofore commercially available as illustrated in FIG. 6 lack the step-ramping facility but may be modified, in accordance with the present invention, to provide step-ramping as described in more detail below.

Figure 7:
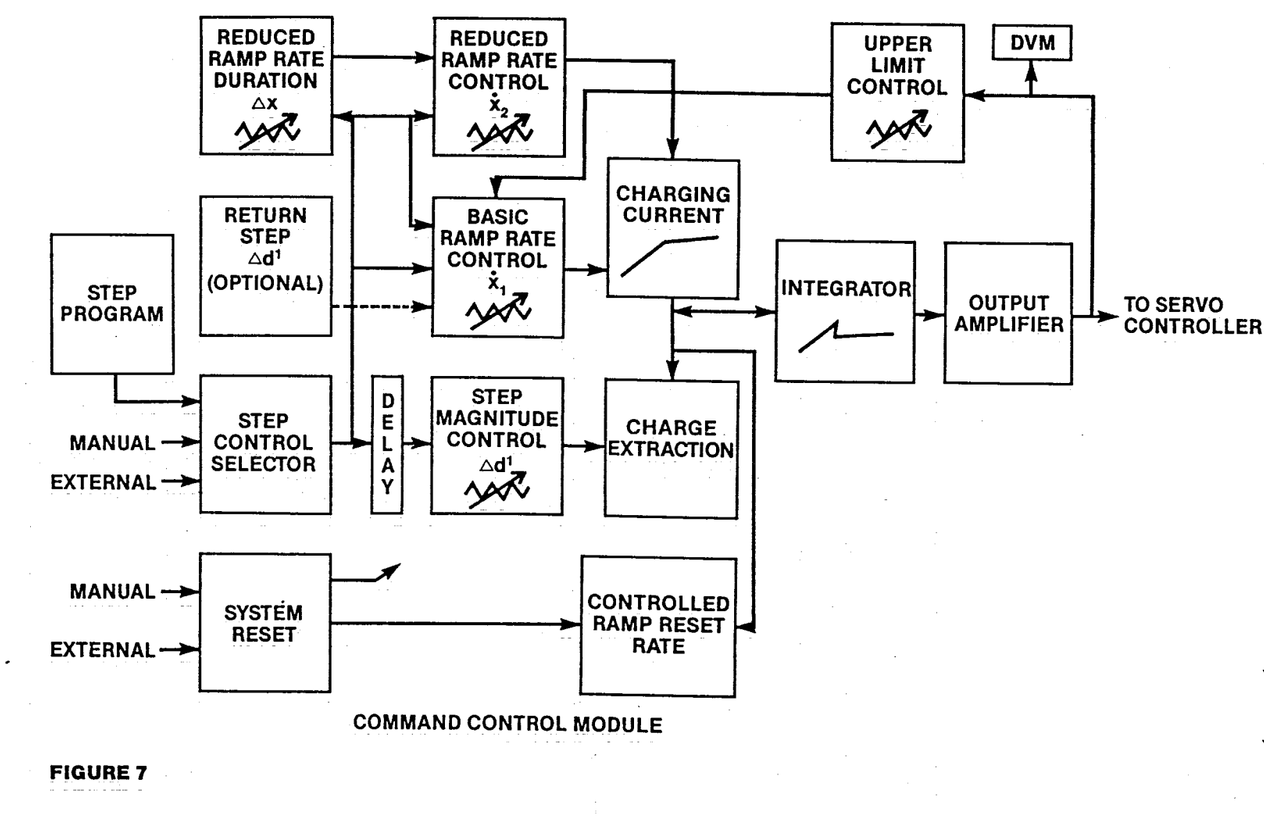
FIG. 7 is a block diagram of the command module of FIG. 6.
Figure 9:
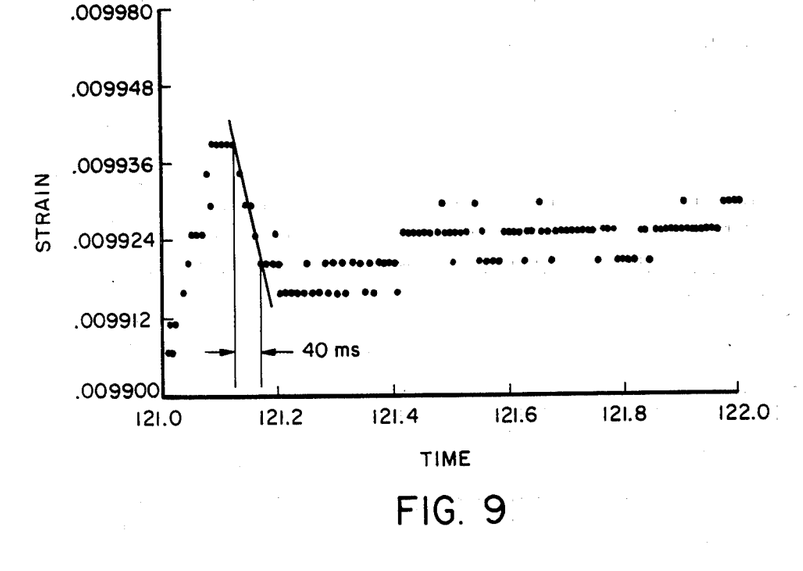
FIG. 9 is a graph of strain versus time for aluminum showing step-ramp plastic strain rate change.
Figure 10:
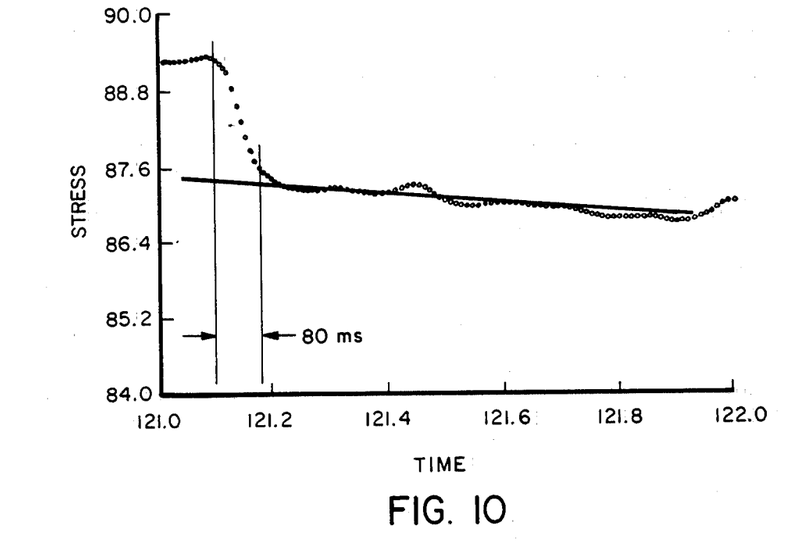
FIG. 10 is a graph showing a corresponding load versus time plot to FIG. 7.

For systems which operate without a computer, a compatible command module as illustrated in FIG. 7 can be added which will manipulate a hydraulic ram in the fashion described with reference to FIG. 1 (finite modulus). It will be noted that the command module used for testing the present system had the following features:

(a) capability to step-ramp and continue at a slow ramp ($10^{-5}S^{-1}$);

(b) resolution of the step height of at least $10^{-5}$ of the total output of the extensometer, so as to eliminate the "digitizing" effect seen in FIG. 9; and (c) the process of step-ramp control can be done by analog or digital control. The digital one as seen in FIG. 10 had a program resolution time of about 40 ms. An analog system may reduce this turn around time below 1 ms but the time is then limied by the inertia of the ram rather than by the program control.

To show that indeed the ram can be made to follow such a pattern (FIG. 1 (finite modulus)), experiments were carried out on a computer controlled servo-hydraulic system. The software was rewritten in such a way so as to direct the ram to ramp at a given strain rate say $+3 \times 10^{-4}S^{-1}$, then upon initiation by the operator, the ram is instructed to change its rate to $-3 \times 10^{-4}S^{-1}$ for 8 ms before resuming a rate of $+1 \times 10^{-5}S^{-1}$. The output of the strain rate and corresponding load response (FIGS. 9 and 10) shows that the step can be imposed during 40 ms. The actual time of 40 ms includes the response time of the digitized control to signal the ram to change speed, change to negative speed and back to positive. With the equipment used the resolution was limited by the analog to digital converter and this was responsible for the discontinuous steps in the value of strain shown in FIG. 9.

In order to assess the strain rate sensitivity (S) of polyethylene pipe, specimens of 35B (by Dupont) resin pipes were tested at various temperatures from $-5°$ to $80°$ C. at strain rates of $3.9 \times 10^{-5}$, $9.75 \times 10^{-5}$ and $9.75 \times 10^{-6}S^{-1}$ using a modified screw driven machine. These tests showed that at elevated temperatures, usually above $40°$ C., the activation volume, v, versus stress, $\sigma$, curve became positive after an initial strain of a few percent.

Figure 11:
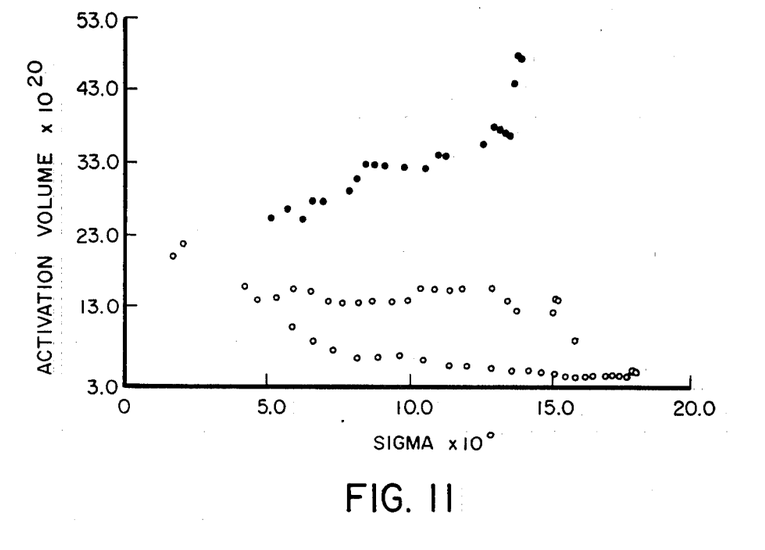
FIG. 11 is a graph showing activation volume versus stress plot for a 35B resin at 3 strain rates.
Figure 12:
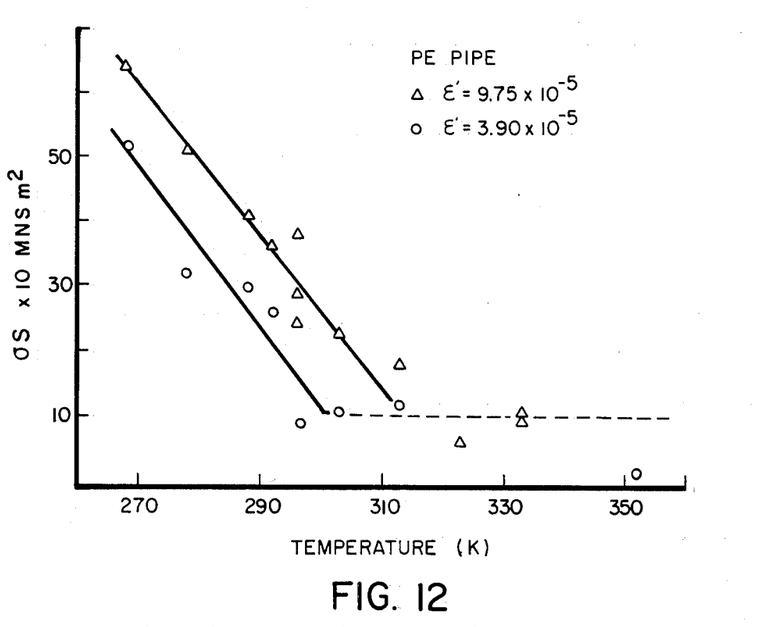
FIG. 12 is a $\sigma$S vs T plot for 35B resin showing transition temperature shift.

The deduction from these results is that for a specific strain rate there is a transition temperature from crystalline behaviour to viscous behaviour. This transition is illustrated in FIG. 12. Note that the transition temperature increases with increase in strain rate. Thus, if one tests at a low enough strain rate at $23°$ C. one should be able to observe the viscous behaviour as shown in FIG. 11 for a strain rate of $9.75 \times 10^{-6}S^{-1}$, and conversely at higher strain rates the crystalline behaviour should dominate.

We claim:

1. A method for precisely controlling plastic strain rate change during plastic deformation testing of a solid material specimen, comprising the steps of:
    (a) applying plastic strain to said specimen, mounted in a testing frame, at a predetermined controlled displacement rate;
    (b) applying an abrupt plastic strain rate change at one or more predetermined strain increments;
    (c) measuring the imposed plastic strain rate change;
    (d) detecting any net change in elastic response of said testing frame, including said specimen, during testing;
    (e) applying an elastic compensating displacement to said testing frame, including said specimen, so that the actual plastic strain rate response of the deforming specimen can be measured; and
    (f) measuring any incremental change of stress required for continuous plastic flow of the specimen upon application of said abrupt change in the plastic strain rate.

2. A method as claimed in claim 1 wherein said solid material is selected from metallic and thermoplastics materials.

3. A method as claimed in claim 1 wherein said corrections are effected by means of a command module associated with an electrohydraulic testing machine controlled by a servo system.

4. An apparatus for precisely controlling plastic strain rate change during plastic deformation testing of a solid material specimen, comprising:
    (a) frame means;
    (b) specimen mounting means for mounting a specimen in said frame meeans for said testing therein;
    (c) plastic strain applying means for applying a plastic strain to said specimen in said frame at a selected controlled displacement rate;
    (d) strain rate change means for applying an abrupt plastic strain rate change at a predetermined strain increment;
    (e) first measurement means for measuring said imposed plastic strain rate change;
    (f) detection means for detecting any net change in elastic response of said frame means, including said specimen, during testing;
    (g) compensation means for precisely compensating for said net change in elastic response so that the actual plastic strain rate response of said non-elastic deforming specimen can be measured; and
    (h) second measurement means for measuring any incremental change of stress required for continuous plastic deformation of said specimen upon abrupt change in the plastic strain rate.

5. Apparatus as claimed in claim 4 wherein said strain rate is effected by an electro-hydraulic system controlled by a servo system.

6. Apparatus as claimed in claim 5 wherein said electro-hydraulic system includes analog or digital command control.

7. Apparatus as claimed in claim 6 wherein said control is digital and amenable to computer control.

* * * * *